(12) United States Patent
Kerrouche et al.

(10) Patent No.: US 11,717,176 B2
(45) Date of Patent: Aug. 8, 2023

(54) SMARTWATCH-TYPE INDIVIDUAL MEDICAL MONITORING DEVICE AND METHOD FOR INDIVIDUAL MEDICAL MONITORING OF A USER THEREOF

(71) Applicants: Samira Kerrouche, Garges-les-Gonesse (FR); Hayame Bouyahia, Franqueville Saint Pierre (FR)

(72) Inventors: Samira Kerrouche, Garges-les-Gonesse (FR); Hayame Bouyahia, Franqueville Saint Pierre (FR)

(*) Notice: Subject to any disclaimer, the term of this patent is extended or adjusted under 35 U.S.C. 154(b) by 215 days.

(21) Appl. No.: 17/239,535

(22) Filed: Apr. 23, 2021

(65) Prior Publication Data

US 2021/0330199 A1 Oct. 28, 2021

(30) Foreign Application Priority Data

Apr. 23, 2020 (FR) ..................... 20 04049

(51) Int. Cl.
*A61B 5/00* (2006.01)
*A61B 5/0205* (2006.01)
(Continued)

(52) U.S. Cl.
CPC ........ *A61B 5/02055* (2013.01); *A61B 5/0022* (2013.01); *A61B 5/024* (2013.01);
(Continued)

(58) Field of Classification Search
CPC .... A61B 2560/0214; A61B 2562/0271; A61B 5/0022; A61B 5/02055; A61B 5/024; A61B 5/026; A61B 5/1112; A61B 5/14532; A61B 5/14542; A61B 5/681; A61B 5/6843; A61B 5/742; A61B 5/746; G16H 10/60; G16H 40/67; G16H 50/30
See application file for complete search history.

(56) References Cited

U.S. PATENT DOCUMENTS

2017/0014035 A1    1/2017 Newberry
2017/0105676 A1    4/2017 Liu
(Continued)

FOREIGN PATENT DOCUMENTS

WO    2018/114180 A1    6/2018

*Primary Examiner* — George Manuel
(74) *Attorney, Agent, or Firm* — Hoffberg & Associates; Steven M. Hoffberg

(57) ABSTRACT

A smartwatch-type individual medical monitoring device includes a main body with a display screen, a bracelet linked to the main body, a processor and a measurement instrument positioned opposite a radial artery of the wrist of the user. The measurement instrument includes a first sensor to continuously measure the oxygen level, a second sensor measures the heart rate by measuring the vibrations of the blood flow at the radial artery, and a third sensor measures the ascending and descending blood flows at the radial artery. The processor is configured to: acquire the measured data of the three sensors, analyze the measured oxygen level, analyze the number of measured vibrations of the blood flow, analyze the measured ascending and descending blood flows, output detection of an anomaly based on analysis of oxygen level, heart rate and ascending and descending blood flows, and store the measured data of the three sensors.

20 Claims, 3 Drawing Sheets

(51) Int. Cl.
*G16H 40/67* (2018.01)
*G16H 10/60* (2018.01)
*G16H 50/30* (2018.01)
*A61B 5/024* (2006.01)
*A61B 5/026* (2006.01)
*A61B 5/11* (2006.01)
*A61B 5/145* (2006.01)

(52) U.S. Cl.
CPC ............ *A61B 5/026* (2013.01); *A61B 5/1112* (2013.01); *A61B 5/14532* (2013.01); *A61B 5/14542* (2013.01); *A61B 5/681* (2013.01); *A61B 5/742* (2013.01); *A61B 5/746* (2013.01); *G16H 10/60* (2018.01); *G16H 40/67* (2018.01); *G16H 50/30* (2018.01); *A61B 2560/0214* (2013.01); *A61B 2562/0271* (2013.01)

(56) References Cited

U.S. PATENT DOCUMENTS

| | | | |
|---|---|---|---|
| 2018/0116560 A1* | 5/2018 | Quinn | ................ A61B 5/02055 |
| 2019/0125259 A1 | 5/2019 | Huang | |
| 2020/0093015 A1* | 3/2020 | Seo | ......................... G06F 1/163 |
| 2020/0093378 A1 | 3/2020 | Lange et al. | |

* cited by examiner

400
SMARTWATCH-TYPE INDIVIDUAL MEDICAL MONITORING DEVICE AND METHOD FOR INDIVIDUAL MEDICAL MONITORING OF A USER THEREOF

RELATED APPLICATION

This application claims priority from French Patent Application No. 20 04049 filed Apr. 23, 2020, which is incorporated herein by reference in its entirety.

TECHNICAL FIELD

The present invention relates to the field of medical monitoring devices. More particularly, the invention relates to a device for monitoring persons, in particular persons having a need for a medical supervision, in the form of a watch intended to be worn by a user at his wrist and adapted to output information indicative of an anomaly in case of danger to the user, in particular in case of a punctual malaise, a more serious health problem or a long-lasting and treated pathology.

BACKGROUND OF THE INVENTION

Monitoring of persons suffering from pathologies, such as chronic pathologies, but also frail persons or all persons wishing so, is important in order to be able to provide a suitable response on time. Conventionally, such a monitoring is done during examinations in specialized centers or in hospitals.

Such a monitoring may further be done directly by a patient, for example in the case of a post-treatment supervision or in the case of a daily supervision for chronic pathologies such as diabetes or a cardiac disease.

To perform such supervisions, there are devices allowing measuring physiological parameters of a patient such as the blood glucose level and the heart rate.

However, in too many cases, the supervision is not done in a quite regular basis for a patient who might forget some measurements or not remember when he has performed a measurement which could have substantially serious consequences.

Furthermore, an irregular supervision of a patient may result in a lag between the treatment to which the patient is subjected and that one that would be necessary.

Moreover, such a supervision is not accurate since, for example for cardiac diseases, the time point at which a measurement outputting information indicative of a physiological anomaly (cardiac arrhythmia, a loss of too many heart beats) may turn out to be essential for a quick and effective take-over of a pathology. However, too many persons (for example elderly people) may be unable to provide sufficiently accurate details on such phenomena that might happen to them. Thus, the response provided to this type of incidents may be inadequate which is not satisfactory.

In addition, a continuous supervision of persons at risk could also save the life of patients and prevent avoidable medical expenses (hospitalization, treatment) by allowing avoiding possible health problems of these persons.

Hence, there is a need to provide a medical monitoring and supervision device that allows providing a reliable continuous supervision so that the patients could benefit from an adequate response to symptoms.

There is also a need to provide such a device that is simple to use and inexpensive to implement, so that the largest number of patients could benefit from it. In particular, it is an objective of the invention to overcome the drawbacks of the prior art.

OBJECT AND SUMMARY OF THE INVENTION

The invention addresses this need by providing a smartwatch-type individual medical monitoring device adapted to come into contact with a wrist of a user, comprising a main body provided with a display screen, a bracelet linked to the main body, and a measurement instrument intended to be positioned opposite a radial artery of the wrist of the user, when the watch is worn by the user, said measurement instrument comprising:
 a first sensor adapted to continuously measure the oxygen level at the radial artery of said user;
 a second sensor adapted to measure the heart rate of said user by measuring the vibrations of the blood flow at said radial artery;
 a third sensor adapted to measure the ascending and descending blood flows at said radial artery;
said device comprising a processor including:
 means for acquiring the measured data of said first sensor, second sensor and third sensor;
 first means for analyzing the oxygen level measured by said first sensor, comparing said value of the oxygen level with respect to a predetermined first threshold;
 second means for analyzing the number of vibrations of the blood flow measured by said second sensor, comparing said value of the heart rate with respect to a predetermined second threshold;
 third means for analyzing the ascending and descending blood flows measured by said third sensor, comparing said value of the ascending blood flow with respect to a predetermined third threshold and of the descending blood flow with respect to a predetermined fourth threshold;
 means for outputting information indicating the detection or the non-detection of an anomaly according to said analysis of said oxygen level, heart rate and ascending and descending blood flows of said user;
 means for storing said measured data of said first sensor, second sensor and third sensor.

Thus, the invention provides a novel and inventive approach allowing solving at least partially some of the drawbacks of the prior art.

In particular, because this individual medical monitoring device could be worn continuously, it allows providing a medical monitoring and supervision device that allows providing a reliable continuous supervision so that the patients could benefit from an adequate response to symptoms.

Moreover, because these measurements are performed at the radial artery of the user, this device allows obtaining reliable data and performing analyses on accurate data.

Furthermore, thanks to the plurality of implemented sensors as well as the processor, the data can also be cross-checked which enhances this reliability.

Furthermore, such an individual medical monitoring device turns out to be simple to use and inexpensive to implement.

According to a feature of at least one embodiment of the invention, said storage means further contain at least one information relating to said user belonging to the group comprising:
 the age of said user;
 anatomical data of said user;
 morphological data of said user;

an ongoing treatment to which said user is subjected;
a pathology of said user;
the medical history of said user;
the blood type of said user;
the ablations undergone by the user;
the major surgeries undergone by the user;
the blood type of the user;
the results of last examinations (blood test, etc.).

Thus, this allows providing data that are even more accurate.

In this instance, according to a feature of at least one embodiment of the invention:
the predetermined first threshold is defined according to said at least one information relating to said user, and/or
the predetermined second threshold is defined according to said at least one information relating to said user, and/or
the predetermined third threshold is defined according to said at least one information relating to said user, and/or
the predetermined fourth threshold is defined according to said at least one information relating to said user.

According to a feature of at least one embodiment of the invention, the device further comprises alert means. Furthermore, if information indicating the detection of an anomaly is output by said output means, said alert means generate an alert message which is transmitted via a communications device to at least one predetermined contact, said predetermined contact being stored in said storage means.

According to a feature of at least one embodiment of the invention, said communications device comprise a port configured to receive a nano SIM card.

Thus, this allows implementing communication means that are simple and accessible to everyone. Furthermore, this allows avoiding possible problems of compatibility of communication means.

According to a feature of at least one embodiment of the invention, said communications device further comprise means for calling in emergency said at least one predetermined contact.

Thus, this allows providing a quick response in case of emergency.

According to a feature of at least one embodiment of the invention, the device further comprises unique identification means.

Therefore, this allows securing the data contained by this device so that these are not accessible to everyone. Furthermore, this allows ensuring that the data actually correspond to a determined person.

According to a feature of at least one embodiment of the invention, the device further comprises means for detecting a set-up of said device on said wrist of said user.

Therefore, this allows avoiding false measurements and therefore false alerts by ensuring that the device is properly in place on the wrist of the user.

According to a feature of at least one embodiment of the invention, the device further comprises a sensor belonging to the group comprising:
a geolocation sensor;
a blood glucose level sensor;
a temperature sensor.

According to a feature of at least one embodiment of the invention, the device further comprises an electric power supply.

Thus, this allows implementing a device that is autonomous from an energy perspective, with possible charging.

The invention also relates to an individual medical monitoring method, said method being adapted to output information indicating the detection or the non-detection of an anomaly, implementing a smartwatch-type individual medical monitoring device adapted to come into contact with a wrist of a user according to any of the aforementioned embodiments, the method comprising the following steps, implemented by said individual medical monitoring device, when said measurement instrument is positioned opposite a radial artery of said wrist of said user:
measurement of the oxygen level of said user at the radial artery of said user, using said first sensor;
measurement of the heart rate of said user by measuring the vibrations of the blood flow at said radial artery, using said second sensor;
measurement of the ascending and descending blood flows at said radial artery, using said third sensor;
analysis of said oxygen level, heart rate and ascending and descending blood flows of said user, so as to transmit instructions to output information indicating the detection or the non-detection of an anomaly;
output of said information indicating the detection or the non-detection of an anomaly;
storage of said measured oxygen level, heart rate and ascending and descending blood flows of said user,
said analysis step comprising the following successive steps:
comparison of the measured oxygen level with respect to a predetermined first threshold;
comparison of the measured heart rate with respect to a predetermined second threshold;
comparison of the value of the ascending blood flow with respect to a predetermined third threshold and of the value of the descending blood flow with respect to a predetermined fourth threshold, and
instruction to output said information indicating the detection of an anomaly if the oxygen level, and/or the heart rate and/or the ascending and/or descending blood flows of said user respectively exceed the first, second, third and fourth thresholds.

According to a feature of at least one embodiment of the method, if information indicating the detection of an anomaly is output by said output means, the method comprises the following successive steps:
generation of an alert message by said alert means;
sending of said generated alert message to said at least one predetermined contact, via said communications device.

According to a feature of at least one embodiment of the method, the latter comprises a prior authentication step.

The invention further relates to a computer program product downloadable from a communication network and/or stored on a microprocessor-readable medium and/or executable by a microprocessor, characterized in that it comprises program code instructions for the execution of an individual medical monitoring method according to any of the aforementioned embodiments, when it is executed on a computer or a mobile terminal.

The invention also relates to a non-transitory terminal-readable storage medium, storing a computer program comprising a set of instructions executable by a computer or a processor to implement the method according to any of the aforementioned embodiments.

BRIEF DESCRIPTION OF THE DRAWINGS

Other objects, features and advantages of the invention will appear clearly on reading the following description, provided as a mere illustrative and non-limiting example, with reference to the figures, amongst which.

DETAILED DESCRIPTION OF EMBODIMENTS OF THE INVENTION

The general principle of the invention is based on the implementation of a smartwatch-type individual medical monitoring device, adapted to come into contact with a wrist of a user, comprising a main body provided with a display screen, a bracelet linked to the main body, and a measurement instrument intended to be positioned opposite a radial artery of the wrist of the user, when the watch is worn by the user, and adapted to indicate the detection or the non-detection of an anomaly according to several criteria that are measured at this radial artery.

Such a watch allows performing a coherent analysis of the vital data thanks to a combination of sensors, and thus determining the condition of a person. For example, this determination may allow performing live diagnostics by rescue services, performing remote consultations, performing monitoring of elderly people.

Such a device may be used to enhance safety and monitoring of persons, more particularly of vulnerable persons.

For example, such an individual monitoring device may be used for monitoring patients having chronic pathologies or having to be subjected to a particular supervision (for example a post-hospitalization supervision). Such a device may also turn out to be useful for the medical supervision of elderly people.

This type of devices turns out to be simple to design and to use.

Figure 1:
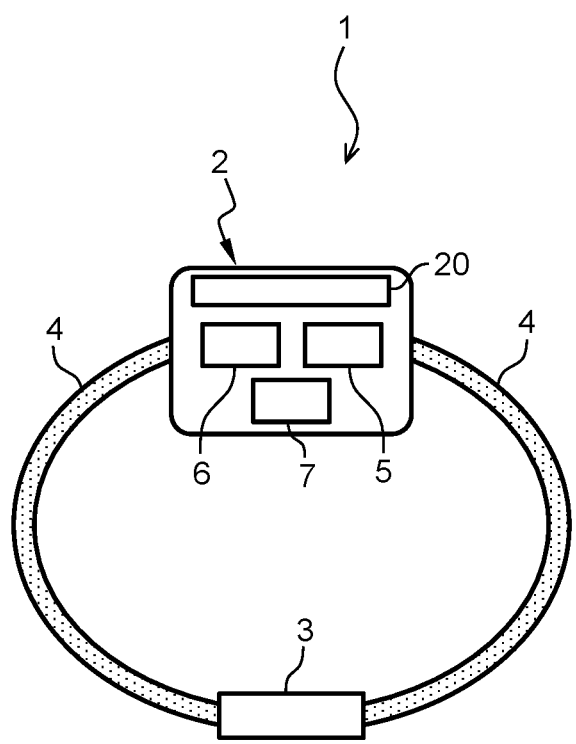
FIG. 1 is a diagram illustrating a side view of a monitoring device according to one embodiment.
Figure 2:
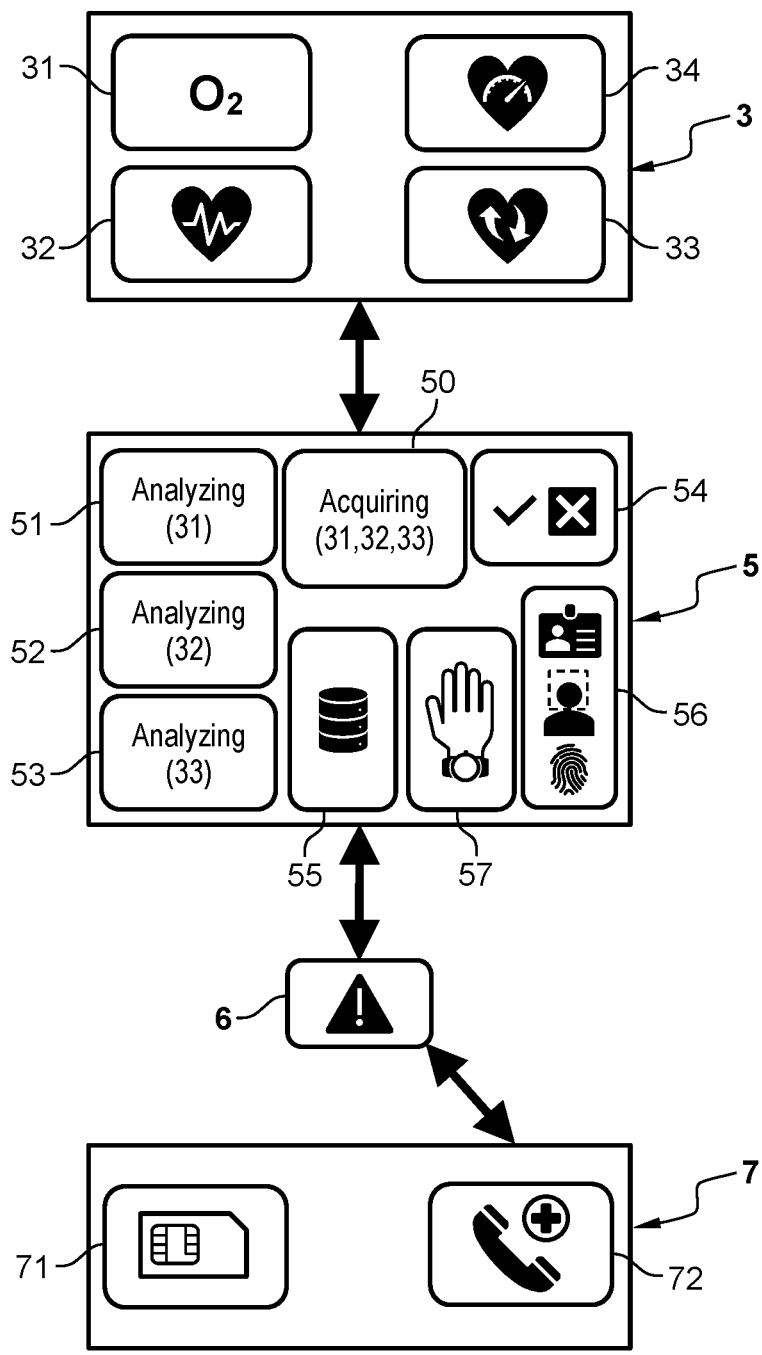
FIG. 2 is a diagram illustrating a measurement instrument and a processor according to an embodiment of the invention.

A first embodiment of the monitoring device according to the invention is now presented with reference to FIGS. 1 and 2.

As illustrated in these figures, the individual medical monitoring device 1 is of the smartwatch type.

It is configured to come into contact with a wrist of a user, so that one of the portions, more particularly the portion of the device where a measurement instrument 3 is housed, could be positioned opposite a radial artery of the wrist of the user, when the watch is worn by this user. This watch further comprises a main body 2 provided with a display screen 20 and a bracelet 4 linked to the main body 2.

In this embodiment, such a main body 2 is made by injected plastic molding so as to provide a material that is tight and resistant to the different conditions in which it might have to evolve, such as water in a shower or in a bathtub (so that the user could keep his smartwatch all the time).

There may also be provided a main body made of another material that allows providing the same resistance and tightness conditions.

The bracelet 4 may also be made by injected plastic molding or of silicone.

For example, this bracelet may have a closure positioned on one side, so as to facilitate placement and removal thereof.

Nonetheless, the bracelet may also consist of a clasp bracelet or a locking bracelet for safety reasons.

It should be noted that the device presented in this embodiment comprises an electric power supply. Such a power supply is herein in the form of a battery, arranged at the processing means 5, which thus enables this device to be autonomous.

According to one embodiment, this battery may be a rechargeable cell or not.

Such a battery may further consist of a LiPO battery enabling a quick charging. This battery may be connected to a USB port allowing charging thereof. Charging may also be done by induction so as to avoid a possible intake of water or dust.

Charging such a battery may also be performed by the Sun, so as to provide an ecological solution.

As described before, the monitoring device comprises a measurement instrument 3. In this embodiment, this measurement instrument 3 comprises:

a first sensor 31 adapted to continuously measure the oxygen level of the user at the radial artery;

a second sensor 32 adapted to measure the heart rate of the user by measuring the vibrations at the radial artery;

a third sensor 33 adapted to measure the ascending and descending blood flows at the radial artery.

In this embodiment, and in order to have a permanent supervision of the user, these measurements are continuously performed.

Of course, where appropriate, it may be provided that either one of these measurements is performed periodically, for example, so as to save the power of the battery of the smartwatch.

It should be noted that the first sensor 31 measures the oxygen level of the user via an element equipped with a light, the oxygen level being assessed afterwards by an algorithm implemented at the processor (presented hereinafter).

For example, this oxygen sensor may implement miniature plethysmography methods.

In this embodiment, the measurement instrument further comprises a blood pressure sensor 34 allowing measuring the blood pressure of the user at the wrist.

It should be noted that, according to an embodiment of the invention, such a device may also be connected to a blood pressure meter so that the blood pressure measurements are taken and kept for a predefined time period. Thus, this would allow having a condition of a patient over this predefined time period. Such a variant may be a complement to the blood pressure sensor, should a check-up of the data is needed.

It should also be noted that such a blood pressure meter may be adapted to communicate with this monitoring device, by conventional wireless communication means.

According to a non-represented embodiment, this measurement instrument may also comprise a sensor allowing detecting a fall of the user, for example an altimeter adapted to detect an abrupt change in altitude (herein, the altitude of the wrist).

According to another non-represented embodiment, the measurement instrument may also comprise a sensor allowing measuring the blood glucose level of the user.

According to another non-represented embodiment, the measurement instrument may also comprise a sensor allowing measuring the temperature of the user.

According to another non-represented embodiment, the device may also comprise a geolocation sensor. Such a sensor may, for example, turn out to be useful in the context of prevention or of action for persons who would suffer from Alzheimer's disease, elderly people, or persons suffering from a psychiatric pathology.

In order to prioritize essential sensors monitoring the vital functions, it should be noted that one or more of the additional sensors may, according to one embodiment, be activated or deactivated by an action of the user, for example by a tactile action on the display screen 20 or through a combination of buttons.

In this embodiment, the measurement instrument 3 is connected, via a cable, which is herein a ribbon cable, to a processor 5 whose function is to analyze the measured parameters and output information indicating the detection or the non-detection of an anomaly according to said analysis.

This processor or processing unit 5 includes herein:
- means 50 for acquiring the measured data of the first sensor 31, second sensor 32 and third sensor 33;
- first means 51 for analyzing the oxygen level measured by the first sensor 31, positioned at the radial artery comparing the value of the oxygen level with respect to a predetermined first threshold;
- second means 52 for analyzing the number of vibrations measured by the second sensor 32, comparing the value of the heart rate with respect to a predetermined second threshold;
- third means 53 for analyzing the ascending and descending blood flows measured by the third sensor 33, comparing the value of the ascending blood flow with respect to a predetermined third threshold and of the descending blood flow with respect to a predetermined fourth threshold, and
- means for outputting 54 information indicating the detection or the non-detection of an anomaly according to the analysis of the oxygen level, heart rate and ascending and descending blood flows of the user.

According to an embodiment of the invention, the means for outputting 54 information indicating the detection or the non-detection of an anomaly according to the analysis of the oxygen level, heart rate and ascending and descending blood flows of the user can output information indicating the detection of an anomaly if at least one of the measured parameters is indicative of an anomaly.

For example, in case of an abrupt drop in the oxygen level, perceivable through the measurement of the oxygen level and then the comparison with respect to a predetermined threshold of the expected oxygen level, the output means could output information indicating the detection of an anomaly.

Furthermore, if the comparison of the value of the ascending blood flow with respect to a predetermined third threshold and/or of the descending blood flow with respect to a predetermined fourth threshold reveals an anomaly, this might be indicative of a cardiac pathology (arrhythmia, tachycardia, bradycardia, or heart trouble), the output means could therefore also output information indicating the detection of an anomaly.

According to another embodiment, and in order to be able to reduce the possibility of a false alert, the output means could output information indicating the detection of an anomaly if at least two of the measured parameters are indicative of an anomaly, that is to say if at least two of the measured parameters are beyond the respective predetermined threshold.

It should be noted that this processor 5 further comprises a storage medium 55 for storing the measured data of the first sensor 31, second sensor 32 and third sensor 33.

Storing the measured data of the first sensor 31, second sensor 32 and third sensor 33 allows keeping a history of vital information of the user over a substantially long period depending on the embodiments. In this manner, a person who consults the history, such as a physician or a nurse, can have a complete overview of the medical history of the user of the watch.

According to one embodiment, the device further comprises means for analyzing the measured data stored over a predefined period, for example to detect possible anomalies, such as a cardiac arrhythmia.

This may also be useful in the context of falls detection, an analysis of the data between two successive measurements may allow detecting an abrupt change in the altitude of the wrist, which might be synonym of a fall.

This may also be useful in the context of diabetes supervision, an analysis of the data between several successive measurements may allow detecting an abrupt change in the sugar content in the blood of the user, which may be synonym of a hypoglycemia or a hyperglycemia.

It should be noted that, according to the embodiment presented herein, the storage medium 55 further contain at least one information relating to the user belonging to the group comprising:
- the age of the user;
- anatomical data of the user;
- morphological data of the user;
- an ongoing treatment to which the user is subjected;
- a pathology of said user;
- the medical history of the user;
- the blood type of the user;
- the ablations undergone by the user;
- the major surgeries undergone by the user;
- the blood type of the user;
- the results of last examinations (blood test, etc.).

In this case, and for the response given to a possible anomaly to be the most suitable as possible, it is preferable that:
- the predetermined first threshold is defined according to said at least one information relating to said user, and/or
- the predetermined second threshold is defined according to said at least one information relating to said user, and/or
- the predetermined third threshold is defined according to said at least one information relating to said user, and/or
- the predetermined fourth threshold is defined according to said at least one information relating to said user.

For example, a heart rate threshold will not be the same if the person is athletic or not, according to his age or his morphology.

Similarly, an ongoing treatment may change the alert criteria. For example, a blood pressure treatment may vary the threshold at which a measured blood pressure turns out to be an anomaly.

It should be noted that, according to one embodiment, this or these information relating to the user may be consulted by displaying on the display screen 20 of the main body 2.

For example, this may be accessible through a combination of keys or by pressing on this display screen.

In this manner, this may allow displaying ongoing medical treatments.

According to one embodiment, one or several information relating to the user may be automatically displayed in case of output of information indicating the detection of an anomaly. For example, such a feature may turn out to be useful in case of intervention of rescue teams who might need to access some data of a patient to be able to quickly intervene.

As illustrated in FIG. 2, the device according to this embodiment further comprises alert means 6. Therefore, if information indicating the detection of an anomaly is output by the output means 54, these alert 6 generates an alert message which is transmitted via the communications device 7 to at least one predetermined contact.

In this instance, the communications device 7 comprise a port 71 configured to receive a SIM card, preferably a nano SIM card.

These communications device means may be accompanied with transmission means implemented in the form of an antenna operating by a wireless technology such as Bluetooth, Wifi, 3G, 4G, or 5G.

In this manner, the alert message may be emitted, for example, in the form of a SMS or a voice message sent on the telephone of a person.

This alert message may also be emitted in the form of a notification on a mobile terminal of the predetermined contact.

This alert message may further be accompanied with an alert sent to rescue services so as to gain in effectiveness for the intervention.

According to one embodiment, the alert message may contain important information on the generated alert, for example the measurement that has generated this alert, information relating to the user (such as a possible ongoing treatment or a pathology).

According to one embodiment, the alert message may also be accompanied with a pre-diagnostic so as to guide a person more easily to the adequate rescue service.

In the presented embodiment, the predetermined contact(s) is/are stored in the storage medium 55.

According to an embodiment of the invention, this predetermined contact may also be automatically displayed on the display screen 20 in case of output of information indicating the detection of an anomaly.

There may be provided an embodiment of the invention wherein the measured data are accessible by the user who, for example by action on the display screen or through a combination of buttons, sends data to a medical practitioner via the communications device 7 so as to be able to perform a remote consultation.

There may also be provided an embodiment wherein the communications device are configured to receive calls, texts and data so that a third-party, for example a medical practitioner, could enter data in a format recognized by the device. In this manner, a medical practitioner could, for example, perform a remote medical prescription, the treatment then being input directly as information relating to the user.

It may also be provided that the monitoring device comprises means for emitting a notification on the digital screen so as to remind the user of a treatment to take or of a scheduled consultation.

Advantageously, the monitoring device according to the presented embodiment further comprises unique identifier 56.

In this manner, this allows securing the device by limiting access to the data and to its use to one or several authorized person(s).

In this instance, the identification of the user is achieved by entering the social security number of the user.

Nonetheless, there may be provided an embodiment wherein the identification means could consist of another means, such as a fingerprint or a facial recognition.

There may also be provided an embodiment wherein these unique identification means comprise a password.

Furthermore, the device according to the presented embodiment comprises means 57 for detecting a set-up of this device on the wrist of the user.

In this manner, this allows avoiding false alerts in case of a suspect measurement while the device is not placed on the wrist of the user.

In the illustrated embodiment, the communications device further comprise means 72 for calling in emergency the predetermined contact.

These emergency call means may be implemented in the form of two buttons placed on either side of the main body, the user having to press simultaneously on both buttons to perform this emergency call.

Such emergency call means may also be implemented in the form of one single button, for example a button placed at a location of the device that is difficult to access so that it could not be used inadvertently.

Figure 3:
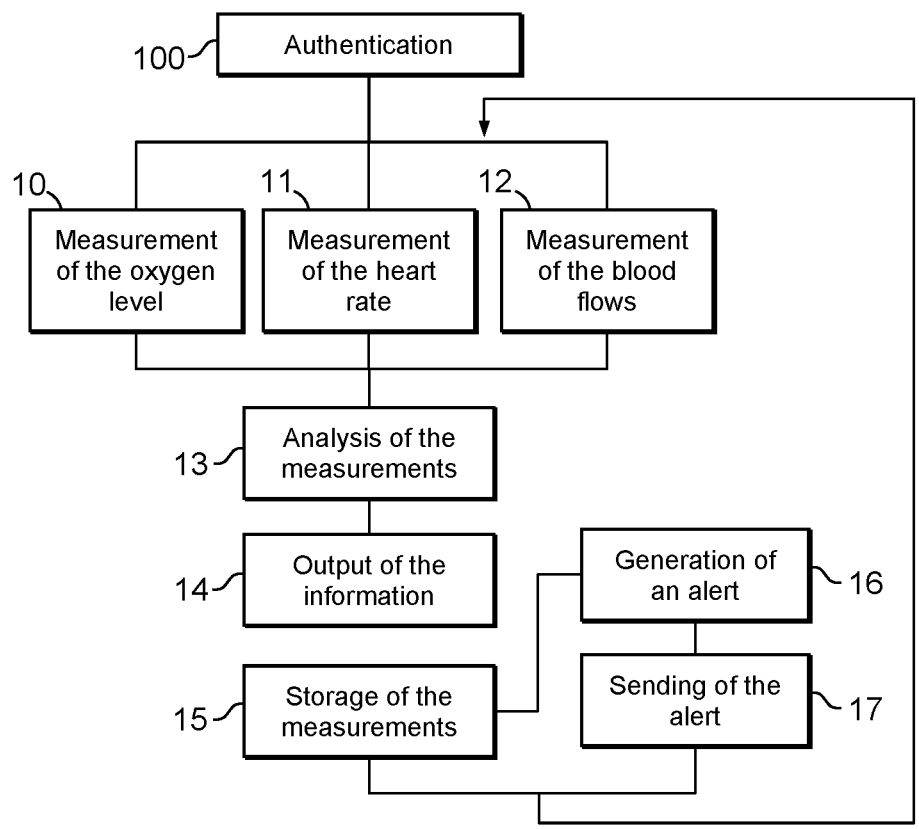
FIG. 3 is a diagram illustrating a method for monitoring a user according to an embodiment of the invention.
Figure 4:
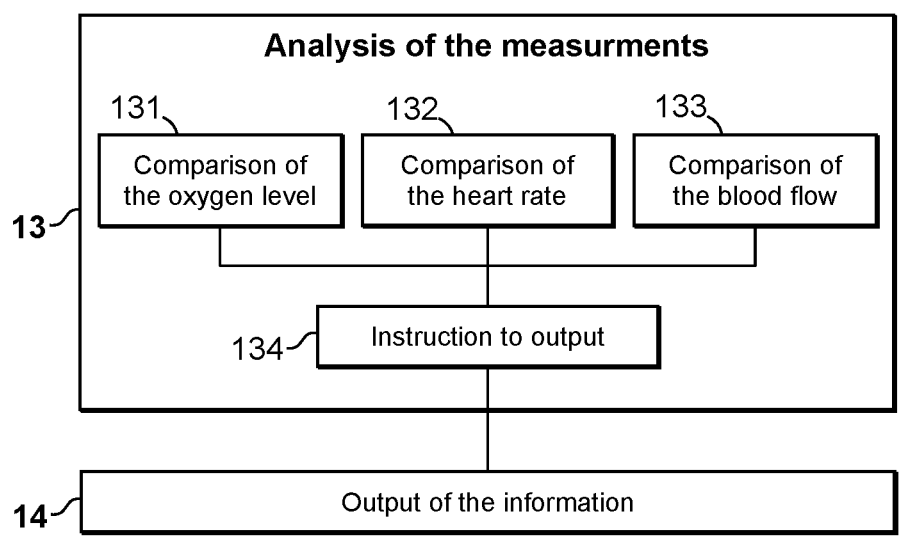
FIG. 4 is a diagram illustrating in detail the analysis step of the supervision method according to the embodiment of FIG. 3.

There is now presented, with reference to FIGS. 3 and 4, an individual medical monitoring method, this method being adapted to output information indicating the detection or the non-detection of an anomaly.

According to the invention, this individual medical monitoring method implements a smartwatch-type individual medical monitoring device 1 adapted to come into contact with a wrist of a user according to any of the aforementioned embodiments.

As illustrated, the method comprises the following steps, implemented by the smartwatch, when the measurement instrument 3 is positioned opposite a radial artery of the wrist of the user:

- measurement 10 of the oxygen level of the user, using said first sensor 31 positioned at the radial artery;
- measurement 11 of the heart rate of the user by measuring the vibrations of the blood flow at the radial artery, using the second sensor 32;
- measurement 12 of the ascending and descending blood flows at the radial artery, using the third sensor 33;
- analysis 13 of the oxygen level, heart rate and ascending and descending blood flows of the user, so as to transmit instructions to output information indicating the detection or the non-detection of an anomaly;
- output 14 of the information indicating the detection or the non-detection of an anomaly;
- storage 15 of the measured oxygen level, heart rate and ascending and descending blood flows of the user.

According to the invention, the analysis step 13 comprises the following successive steps:

- comparison 131 of the measured oxygen level with respect to a predetermined first threshold;
- comparison 132 of the measured heart rate with respect to a predetermined second threshold;
- comparison 133 of the value of the ascending blood flow with respect to a predetermined third threshold and of the value of the descending blood flow with respect to a predetermined fourth threshold, and
- instruction to output 134 the information indicating the detection of an anomaly if the oxygen level, and/or the heart rate and/or the ascending and/or descending blood flows of the user respectively exceed the first, and/or second, and/or third and/or fourth thresholds.

According to an embodiment of the invention, the step of instructing the output 14 of information indicating the detection or the non-detection of an anomaly according to the analysis of the oxygen level, and/or heart rate and/or ascending and/or descending blood flows of the user can output information indicating the detection of an anomaly if at least one of the measured parameters is indicative of an anomaly.

For example, in case of an abrupt drop in the oxygen level, perceivable through the measurement of the oxygen level and then the comparison with respect to a predetermined threshold of the expected oxygen level, the output means could output information indicating the detection of an anomaly.

Furthermore, if the comparison of the value of the ascending blood flow with respect to a predetermined third threshold and/or of the descending blood flow with respect to a predetermined fourth threshold reveals an anomaly, this might be indicative of a cardiac pathology (arrhythmia, tachycardia, bradycardia, or heart trouble), the output means could therefore also output this information indicating the detection of an anomaly.

According to another embodiment, and in order to be able to reduce the possibility of a false alert, the output step adapted to output information indicating the detection of an anomaly could be performed if at least two of the measured parameters are indicative of an anomaly, that is to say if at least two of the measured parameters are beyond the respective predetermined threshold.

In the embodiment of the method illustrated in FIG. 3, if information indicating the detection of an anomaly is output by the output means 54, the method comprises the following successive steps:

generation 16 of an alert message by the alert 6;
sending 17 of the generated alert message to the predetermined contact, via the communications device.

Furthermore, in the illustrated embodiment, the method comprises a prior authentication step 100. In this manner, this allows securing the device by limiting access to the data and to the use thereof to one or several authorized person(s).

The invention also relates to a computer program product downloadable from a communication network and/or stored on a microprocessor-readable medium and/or executable by a microprocessor, comprising program code instructions for the execution of an individual medical monitoring method according to any of the aforementioned embodiments, when it is executed on a computer.

The invention also relates to a non-transitory computer-readable storage medium, storing a computer program comprising a set of instructions executable by a computer or a processor to implement the individual medical monitoring method according to any of the aforementioned embodiments.

More particularly, the storage medium may be included in the main body, for example in the memory 55 embedded within the processor. It may also be included within the measurement instrument.

According to one embodiment, it may be provided that the device and the method are accompanied with the creation of an associated card for a reader (for example a SD card or a chip card that would also contain all of the information stored in the embedded memory. Such a data duplication may be done through an online synchronization or via the communications device.

It may be further provided that such an associated card could be used in connection with a software allowing synchronizing the whole so as to generate a complete medical file for a patient (including for example the invariable information of the patient, the detail of the medical history of the patient, a record of the specified prescriptions, radiology results, blood tests results enabling an immediate reading of a situation relating to the patient).

For example, it may be provided that the software allows automatically having the transmission of the information per category between the laboratory and one or several physician(s) and an overall synthesis of blood data on a monthly basis and even a yearly basis, without having to carry out any paper review.

It may also be provided that the update of the examinations could be directly transmitted by the physician to the user, for example after validation by the user of access to his smartwatch to save this information.

There may further be provided means for synchronization between the monitoring device, the associated card, and the complete medical file of the patient stored in a database.

It may also be provided that such a device comprises a maintenance schedule, so that the offered functions remain optimal and the medical supervision is reliable for a given user.

The invention claimed is:

1. A smartwatch-type individual medical monitoring device configured to come into contact with a wrist of a user, comprising:

a main body provided with a display screen;
a bracelet linked to the main body;
a measurement instrument configured to be positioned opposite a radial artery of the wrist of the user, when the medical monitoring device is worn by the user, the measurement instrument comprising:
a first sensor configured to continuously measure an oxygen level at the radial artery of the wrist of the user;
a second sensor configured to measure a heart rate of the user by measuring vibrations of a blood flow at the radial artery of the wrist of the user;
a third sensor configured to measure ascending and descending blood flows at the radial artery of the wrist of the user;
a processor configured to:
acquire the measured data of the first sensor, second sensor and third sensor;
analyze the oxygen level measured by the first sensor and compare a measured value of the oxygen level to a first predetermined threshold;
analyze a number of vibrations of the blood flow measured by the second sensor and compare a value of the heart rate to a second predetermined threshold;
analyze the ascending and descending blood flows measured by the third sensor, compare a value of the ascending blood flow to a third predetermined threshold and compare a value of the descending blood flow to a fourth predetermined threshold; and
output on the display screen information indicating a detection or a non-detection of an anomaly in accordance with the analysis of the oxygen level, the heart rate and the ascending and descending blood flows of the user; and
wherein the processor comprises a storage medium to store the measured data of the first sensor, the second sensor and the third sensor.

2. The medical monitoring device of claim 1, wherein the storage medium is configured to store at least one information relating to the user belonging to a group comprising: an age of said user; anatomical data of the user; morphological data of the user; an ongoing treatment to which the user is subjected; a pathology of the user; a medical history of the user; a blood type of the user; ablations undergone by the user; major surgeries undergone by the user; and results of last examinations.

3. The medical monitoring device of claim 2, wherein at least one of the following:
the first predetermined threshold is defined according to said at least one information relating to the user,
the second predetermined threshold is defined according to said at least one information relating to the user,
the third predetermined threshold is defined according to said at least one information relating to the user, and
the fourth predetermined threshold is defined according to said at least one information relating to the user.

4. The medical monitoring device of claim 1, further comprising an alert device configured to generate an alert message in response to output of the information indicating the detection of the anomaly, the alert message being transmitted via a communications device to at least one predetermined contact, said at least one predetermined contact being stored in the storage medium.

5. The medical monitoring device of claim 4, wherein the communications device comprises a port configured to receive a nano SIM card.

6. The medical monitoring device of claim 4, wherein the communications device is configured to call said at least one predetermined contact in an emergency.

7. The medical monitoring device of claim 1, wherein the processor is configured to identify the user by a unique identifier.

8. The medical monitoring device of claim 1, wherein the processor is configured to detect a set-up of the medical monitoring device on the wrist of the user.

9. The medical monitoring device of claim 1, further comprising at least one of the following sensors: a geolocation sensor, a blood glucose level sensor and a temperature sensor.

10. The medical monitoring device of claim 1, further comprising an electric power supply.

11. An individual medical monitoring method for outputting information indicating a detection or a non-detection of an anomaly, implementing a smartwatch-type individual medical monitoring device of claim 1, the method comprising:
placement of the measurement instrument opposite the radial artery of the wrist of the user;
measurement of the oxygen level of the user by the first sensor;
measurement of the heart rate of the user by measuring the vibrations of the blood flow of the user using the second sensor;
measurement of the ascending and descending blood flows of the user by the third sensor;
analysis of the oxygen level, the heart rate and the ascending and descending blood flows of the user by the processor configured successively to:
compare the oxygen level to the first predetermined first threshold;
compare the heart rate to the second predetermined second threshold; and
compare the value of the ascending blood flow to the third predetermined threshold and compare the value of the descending blood flow to the fourth predetermined threshold;
transmission of instructions to output information indicating the non-detection of the anomaly or the detection of the anomaly in response to at least one of the following: the oxygen level exceeds the first predetermined threshold, the heart rate exceeds the second predetermined threshold, the ascending blood flows exceed the third predetermined threshold and the descending blood flows exceed the fourth predetermined threshold;
output on the display screen the information indicating the detection or the non-detection of the anomaly; and
storage of the oxygen level, the heart rate and the ascending and descending blood flows of the user in the storage medium.

12. The individual medical monitoring method of claim 11, wherein in response to the output of the information indicating the detection of the anomaly, further comprising successively:
generation of an alert message; and
transmitting the alert message to said at least one predetermined contact via a communications device.

13. The individual medical monitoring method of claim 11, further comprising a prior authentication of the user.

14. A computer program product downloadable from a communication network executable by a microprocessor of a computer or mobile terminal, comprising program code instructions for implementing the individual medical monitoring method of claim 11.

15. A computer program product recorded on a microprocessor-readable non-transitory medium executable by a microprocessor of a computer or mobile terminal, comprising program code instructions for implementing the individual medical monitoring method of claim 11.

16. A computer program recorded on a non-transitory terminal-readable storage medium, comprising a set of instructions executable by a computer or a processor to implement the individual medical monitoring method of claim 11.

17. A smartwatch device, comprising:
a display housing attached to a bracelet;
a display screen in the display housing;
a memory;
a sensor housing disposed in the bracelet positioned opposite a radial artery in the wrist of a wearer, when the medical monitoring device is worn by the user, the sensor housing comprising:
a blood oxygen sensor configured to continuously measure a blood oxygen level of the wearer;
a heart rate sensor configured to measure a heart rate of the wearer;
a blood flow sensor configured to measure ascending and descending blood flows at the radial artery in the wrist of the wearer; and
at least one automated processor configured to:
compare the blood oxygen level to a first predetermined threshold, the heart rate to a second predetermined threshold, a value of the ascending blood flow to a third predetermined threshold, and a value of the descending blood flow to a fourth predetermined threshold;
output on the display screen information indicating a detection of an anomaly selectively dependent on the comparisons of the oxygen level, the heart rate and the ascending and descending blood flows of the wearer; and
store information corresponding to at least a portion of the oxygen level, the heart rate and the ascending and descending blood flows of the wearer in the memory.

18. The smartwatch device according to claim 17, further comprising a transmitter configured to communicate an alert message in response to the detected anomaly.

19. The smartwatch device according to claim 18, wherein the transmitter is configured to receive a nano SIM card, and to call at least one predetermined contact in response to the detected anomaly.

20. A smartwatch, comprising:
- a sensor housing disposed in a bracelet, the bracelet being configured to position the sensor housing adjacent to a radial artery of a wearer, the sensor housing comprising:
  - a blood oxygen sensor configured to continuously measure a blood oxygen level of the wearer;
  - a heart rate sensor configured to measure a heart rate of the wearer;
  - a blood flow sensor configured to measure ascending and descending blood flows at the radial artery in the wrist of the wearer; and
- at least one automated processor configured to:
  - compare the blood oxygen level to a first predetermined threshold, the heart rate to a second predetermined threshold, a value of the ascending blood flow to a third predetermined threshold, and a value of the descending blood flow to a fourth predetermined threshold; and
  - output an anomaly indication selectively dependent on the comparisons of the oxygen level, the heart rate and the ascending and descending blood flows of the wearer.

* * * * *